United States Patent [19]

Swedo et al.

[11] Patent Number: 5,008,262

[45] Date of Patent: Apr. 16, 1991

[54] METHOD OF TREATING TRICHOTILLOMANIA AND ONCHYPHAGIA

[75] Inventors: Susan E. Swedo, Lorton, Va.; Judith L. Rapoport; Henrietta L. Leonard, both of Washington, D.C.

[73] Assignee: The United States of America as represented by the Department of Health and Human Services, Washington, D.C.

[21] Appl. No.: 207,617

[22] Filed: Apr. 19, 1988

[51] Int. Cl.$^5$ .......................................... A61K 31/395
[52] U.S. Cl. ................................ 514/217; 514/219; 514/563
[58] Field of Search ............................ 514/219, 217

[56] References Cited

U.S. PATENT DOCUMENTS

| | | | |
|---|---|---|---|
| 4,596,799 | 6/1986 | Wasley | 514/219 |
| 4,710,504 | 12/1987 | Baldwin | 514/219 |
| 4,761,411 | 8/1988 | Glamkowski et al. | 514/219 |

OTHER PUBLICATIONS

Current Therapy, 1979, p. 578.
Cecil Textbook of Medicine, 1983, pp. 1992 to 1995.
Medical Dictionary, Saunders, 23rd edition, 1962, p. 948.
Insel et al., Arch. Gen. Psychiatry, 40, pp. 605–612, (1983).
Thoren et al., Arch. Gen. Psychiatry, 37, pp. 1281–1285, (1980).
Montgomery, Pharmaceutical Medicine, 1(2), pp. 189–193, (1980).
Flament et al., Arch. Gen. Psychiatry, 42, pp. 977–983, (1985).
Ananth et al., Prog. Neuro-Psychopharmacol., 5, pp. 257–262, (1981).
Diagnostic and Statistical Manual of Mental Disorders, 3rd edition, pp. 7–9, 321–328, 235–253, (1987).
Sticher et al., Cutis, vol. 26, pp. 90–101, (1980).
Swedo et al., New England Journal of Medicine, 321: p. 497–501, (1989).
Am. Psyc. Assn., 143rd Ann. Meeting, Abstracts:NR11, NR295, and NR327, pp. 50, 159, 173, May 12–17, 1990.
Primeau et al., Canadian Journal of Psychiatry, vol. 32, pp. 699–700, (1987).

*Primary Examiner*—Dale R. Ore
*Attorney, Agent, or Firm*—John E. Tarcza

[57] ABSTRACT

The instant invention is drawn to the use of clomipramine for treating trichotillomania and onchyphagia.

8 Claims, No Drawings

METHOD OF TREATING TRICHOTILLOMANIA AND ONCHYPHAGIA

BACKGROUND OF THE INVENTION

Trichotillomania is a common disorder characterized by plucking of hairs from head, eyelashes, eyebrows and, less commonly, from other parts of the body. While this behavior may rarely accompany classical obsessive compulsive disorder (OCD), the condition is not considered to be a part of OCD and usually is the only disorder present. Similarly onchyphagia (pathologic nail biting) may occasionally co-exist with OCD. However, most nail-biters do not show the obsessive compulsive disorder pattern of behavior and it is considered an independent entity. The *Diagnostic and Statistical Manual of Mental Disorders*, published by the American Psychiatric Association, Washington, 1987, describes compulsions occurring in OCD as "repetitive, " purposeful, and intentional behaviors that are performed in response to an obsession, according to certain rules or in a stereotyped fashion, while trichotillomania is defined as "recurrent failure to resist impulses to pull out one's hair, resulting in noticeable hair loss." DSM-III distinguishes between the two separate disorders suggesting a different etiology, natural history, and treatment response. Onchyphagia is not listed at all in DSM-III as a mental disorder. When onchyphagia and/or trichotillomania are present, self-consciousness about the behavior itself and the resulting disfigurement causes significant distress.

Several methods of treating hair-pulling and nail-biting have been tried heretofore including psychotherapy, behavior modification, hypnosis, relaxation therapy, and administration of varied pharmaceutical preparations. Beauticians have provided skin, hair, and nail treatments at high cost to patients While some of these approaches have proven to be efficacious in specific populations, no treatment has proven to be effective in treating a wide range of patients wherein the common problem pattern is trichotillomania or onchyphagia.

The 5-(3-dimethylaminopropyl)-10, 11-dehydro-5H-dibenzazepines of the formula

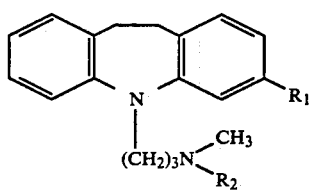

FIG. 1 $R_1$ = H, Cl $R_2$ = H, $CH_3$ have long been used as antidepressants. Yaryura-Tobias, et al. (Current therapeutic Research Vol. 20, No. 4, pp. 541-548), in 1976, described the use of clomipramine (compound of FIG. 1 where R=Cl) for treatment of classical obsessive compulsive neurosis. In 1985, Krishnan, et al. published a review in which use of chlorpromazine, an antipsychotic drug unrelated to clomipramine, was suggested for use in treatment of trichotillomania if the hair-pulling resulted from schizophrenia or obsessive compulsive disorder. There has been no indication this drug should be used in treatment of primary trichotillomania.

Finally, the use of clomipramine in obsessive compulsive patients was believed by many authorities to be of value in treating OCD but only in patients having OCD accompanied by depression. For example, Marks and his associates stated, "When depression is minimal, clomipramine has no demonstrable value.... Clomipramine effects mood more than rituals." (Brit. J. Psychiat. (1980) 136, pp. 1-25 at 22. Others have found clomipramine's antiobsessional effect to be independent of its antidepressant activity.

DESCRIPTION OF THE INVENTION

It has now been discovered that clomipramine is effective in treating trichotillomania or onchyphagia which does not accompany schizophrenia, obsessive compulsive disorder, or depression. The eight patients who responded to the use of clomipramine in the manner described herein had previously undergone both psychotherapy and pharmaceutical therapy used in treatment of depression and/or OCD, to no avail.

The result of therapy on a group of patients with trichotillomania when given clomipramine (FIG. 1), designated CMI, and desipramine (FIG. 1, R=H1, R2=H), designated DMI, was studied. (See Table I). The response to previous therapies had been minimal.

TABLE I

| Pt. No. | Age | Treatment | Baseline score** | CMI score | DMI score |
|---|---|---|---|---|---|
| 1 | 24 yr. | Librium, desaryl, Behavioral modification | 20 | 0 | — |
| 2 | 23 yr. | Behavioral modification, Relaxation | 20 | 10 | — |
| 3 | 25 yr. | Aversion therapy Hypnosis | 11 | 7 | 14 |
| 4 | 16 yr. | Psychotherapy | 23 | 21 | 7* |
| 5 | 23 yr. | Elavil Centrex Behavioral modification Psychotherapy | 20 | 14 | 16 |
| 6 | 23 yr. | Tofranil Xanax Psychotherapy | 18 | 0 | 18 |
| 7 | 21 yr. | Behavioral modification Psychotherapy | 15 | 12 | 14 |
| 8 | 8 yr. | Xanax Psychotherapy Inpatient therapy | 17 | 14 | 19 |

All scores shown are total trichotillomania score.
* = subsequently relapsed and responded to CMI with score = 5

This patient, a 31-year old woman, reported no improvement during the clomipramine trial. However, after the course of treatment was completed, she indicated she had not taken medication as directed and reported results in accord with the degree of side effects rather than therapeutic benefit. She later retried treatment with clomipramine, which resulted in marked improvement.

It had been noted (by our group) that pathologic nail-biters suffering classical obsessive compulsive disorder (OCD) frequently showed a decrease in nail-biting as well as decrease in other compulsive behaviors while taking clomipramine. However, no effective pharmaceutical treatment for persons displaying pathological nail-biting, alone (without depression or OCD), was known.

Two patients whose only behavior problem was nail-biting responded to an open trial of clomipramine therapy, when administered at 250 mg daily. One patient had numerous failures to respond positively to behavior modification. Another, who had suffered from onchyphagia for ten years without remission and who showed no clinical evidence of OCD cleared nail-biting after three weeks.

Clomipramine may be administered as pharmaceutically acceptable salt, if desired. The hydrochloride salt is particularly preferred.

The preferred dosage is 10-250 mg/day. The medication may be given orally or parenterally. The drug may be formulated with usual fillers or carriers known to those of ordinary skill in the art of drug formulation. Oral dosage forms are preferred, as they are easily self-administered on an outpatient basis. The dosage may be administered daily or may be divided for administration 2-6 times daily. Spansules may be prepared for slow release in the gastrointestinal tract.

What we claim is:

1. A method of preventing nail biting by administration of about 10-300 mg/day of clomipramine to a patient suffering from onychophagia which does not accompany schizophrenia, obsessive compulsive disorder or depression.

2. The method of claim 1 wherein the clomipramine is given orally.

3. A method of preventing hair pulling by administration of about 10-300 mg/day of clomipramine to a patient suffering from trichotillomania which does not accompany schizophrenia, obsessive compulsive disorder or depression.

4. The method of claim 3 wherein the clomipramine is given orally.

5. A method of claim 1 wherein the patient suffering from onychophagia is without symptoms of schizophrenia, obsessive compulsive disorder or depression.

6. The method of claim 5 wherein the clomipramine is given orally.

7. A method of claim 3 wherein the patient suffering from trichotillomania is without symptoms of schizophrenia, obsessive compulsive disorder or depression.

8. The method of claim 7 wherein the clomipramine is given orally.

* * * * *